(12) United States Patent
Varcoe

(10) Patent No.: US 9,560,986 B2
(45) Date of Patent: Feb. 7, 2017

(54) MAGNETOMETER FOR MEDICAL USE

(71) Applicant: UNIVERSITY OF LEEDS, Leeds (GB)

(72) Inventor: Benjamin Thomas Hornsby Varcoe, Leeds (GB)

(73) Assignee: University of Leeds, Leeds (GB)

( * ) Notice: Subject to any disclaimer, the term of this patent is extended or adjusted under 35 U.S.C. 154(b) by 147 days.

(21) Appl. No.: 14/409,792

(22) PCT Filed: Jul. 1, 2013

(86) PCT No.: PCT/GB2013/051740
§ 371 (c)(1),
(2) Date: Dec. 19, 2014

(87) PCT Pub. No.: WO2014/006387
PCT Pub. Date: Jan. 9, 2014

(65) Prior Publication Data
US 2015/0150475 A1 Jun. 4, 2015

(30) Foreign Application Priority Data
Jul. 2, 2012 (GB) .................................. 1211704.0

(51) Int. Cl.
*A61B 5/05* (2006.01)
*A61B 5/04* (2006.01)
*G01R 33/00* (2006.01)

(52) U.S. Cl.
CPC ............ *A61B 5/05* (2013.01); *A61B 5/04005* (2013.01); *A61B 5/04007* (2013.01); *G01R 33/0023* (2013.01); *A61B 5/04008* (2013.01); *A61B 2562/0223* (2013.01)

(58) Field of Classification Search
CPC ..... A61B 5/05; A61B 5/04007; A61B 5/7239; A61B 5/743; A61B 5/02; A61B 5/0402
See application file for complete search history.

(56) References Cited

U.S. PATENT DOCUMENTS 4,673,827 A 6/1987 Sommer
5,767,668 A 6/1998 Durand
(Continued)

FOREIGN PATENT DOCUMENTS

EP 1541083 A2 6/2005
WO WO2011/057274 5/2011
WO WO2011057274 5/2011

OTHER PUBLICATIONS

Chinese Office Action dated Dec. 18, 2015, Chinese Patent Application No. 201380035185.3.
(Continued)

*Primary Examiner* — Joel Lamprecht
(74) *Attorney, Agent, or Firm* — Vierra Magen Marcus LLP

(57) ABSTRACT

A medical magnetometer 10 comprising one or more induction coils 2 for detecting a time varying magnetic field of a region of a subject's body, such as the heart. Each coil has a maximum outer diameter of 4 to 7 cm, and a configuration such that the ratio of the coil's length to its outer diameter is at least 0.5, and the ratio of the coil's inner diameter to its outer diameter is 0.5 or less.

Each induction coil 2 is coupled to a respective detection circuit comprising a low impedance pre-amplifier 3, a low pass filter 5, a notch filter 6 to remove line noise, and an averaging element 7. Each detection circuit produces an output signal 9 for use to analyze the time varying magnetic field of the region of the subject's body.

17 Claims, 14 Drawing Sheets

Brooks Coil

(56) References Cited

U.S. PATENT DOCUMENTS

2001/0029329 A1    10/2001   Avrin
2009/0230953 A1     9/2009   Lee

OTHER PUBLICATIONS

B.J. Williamson, et al., "Biomagnetism," Journal of Magnetism and Magnetic Materials, vol. 22, No. 2, 129-201, 1981.
Japanese Decision to Grant dated Apr. 19, 2016, Japanese Patent Application 2015-519349.
Search Report and Written Opinion dated Jan. 9, 2015, Singapore Patent Application No. 11201500018W.
Grosz A. and Paperno E., Analytical optimization of low frequency search coil magnetometers. IEEE Sensors Journal, Jun. 1, 2012, vol. 12, No. 8, pp. 2719-2723, Table 1; Figures 1 and 2.
Deng, K, et al., "Design and development of a pulsed electromagnetic micro-actuator for 3D virtual tactile displays", Mechatronics, Pergamon Press, Oxford, GB., vol. 20. No. 4., Jun. 1, 2010, pp. 503-509.
Slawomir Tumanski, "Review Article; Induction coil sensors—a review", Measurement Science and Technology, IOP, Bristol, GB, vol. 18. No. 3., Mar. 1, 2007, pp. R31-R46.
Williamson, S J, et al., "Biomagnetism", Journal of Magnetism and Magnetic Materials, Elsevier Science Publishers, Amsterdam, NL, vol. 22. No. 2., Jan. 1, 1981, pp. 129-201.
International Search Report dated Aug. 19, 2013, PCT Patent Application PCT/GB2013/051740.
GB Search Report dated Oct. 25, 2012, GB Patent Application GB1211704.0.
IEEE Transactions on Magnetics, vol. 45, No. 6, IEEE, New York, Kunihisa Tashiro et al, "An Experimental Study of Stable Operating Conditions for a High-Sensitivity Induction Gradiometer", pp. 2784 to 2787.

MAGNETOMETER FOR MEDICAL USE

This application is a U.S. national stage filing of International Application No. PCT/GB2013/051740, filed Jan. 1, 2013, which claims priority to GB Patent Application No. 1211704.0, filed on Jul. 2, 2012, entitled "Magnetometer for Medical Use."

BACKGROUND

The technology described herein relates to a magnetometer for medical use, such as for use as a cardiac magnetometer.

It can be useful in many medical situations to be able to measure magnetic fields relating to or produced by the human body. For example, magnetic field measurements can be useful for diagnosing and investigating bladder conditions, foetal abnormalities, pre-term labour, and the heart, and for encephalography.

It is known, for example, that measurements of the magnetic field of the heart can provide useful information, for example for diagnostic purposes. For example, the heart's magnetic field contains information that is not contained in an ECG (Electro-cardiogram), and so a magnetocardiogram scan can provide different and additional diagnostic information to a conventional ECG.

Modern cardiac magnetometers are built using ultra-sensitive SQUID (Superconducting Quantum Interference Device) sensors having a noise floor between 1-1000 $fT/\sqrt{Hz}$. Such devices perform well and have a sound-diagnostic capability.

However, SQUID magnetometers are very expensive to operate as they require cryogenic cooling. Their associated apparatus and vacuum chambers are also bulky pieces of equipment. This limits the suitability of SQUID magnetometers for use in a medical environment, for example because of cost and portability considerations.

Another known form of magnetometer is an induction coil magnetometer. Induction coil magnetometers have the advantage over SQUID magnetometers that cryogenic cooling is not required, they are relatively inexpensive and easy to manufacture, they can be put to a wide range of applications and they have no DC sensitivity.

However, induction coil magnetometers have not been adopted for magneto-cardiography. This is because magneto-cardiography requires low field (<nT), low frequency (<100 Hz) sensing, and existing induction coil magnetometer designs that can achieve such sensitivities are too large to be practical for use as a cardiac probe.

For example, when looking to design a very sensitive induction coil magnetometer, the conventional approach would be to try to maximise the inductance of the coil. The Brooks coil (which is defined, for example, in: Grover, F. W.; Inductance calculations, working formulas and tables; 1946: D. Van Nostrand) is a well-known design of induction coil that maximises the inductance for a given length of wire. The Brooks coil recognises and teaches that the optimum value of the induction will be obtained with a coil having a square winding cross-section with the sides of the square equal to the radius of the core. FIG. 1 illustrates this and shows the configuration of a Brooks coil: a square winding cross-section having a diameter (a side-length) a, with the core radius also being a. However, a coil of this configuration that has the sensitivity needed for magneto-cardiography will then have a diameter that is too large to provide the spatial resolution that is needed for magneto-cardiography.

Thus the literature currently teaches away from using induction coil magnetometers for magnetocardiography, notwithstanding their apparent advantages over SQUID sensors, as it is not believed possible to achieve a sufficiently sensitive induction coil magnetometer whilst still achieving sufficient spatial resolution to be medically useful.

The Applicants believe therefore that there remains scope for improvements to the design and use of magnetometers for medical use, and in particular for cardio-magnetic imaging. In particular, a compact, portable and relatively inexpensive device that can image magnetic fields of the human body, such as the magnetic field of the heart, would provide a number of significant advantages over existing medical and cardiomagnetometer designs.

BRIEF DESCRIPTION OF THE DRAWINGS

A number of embodiments of the technology described herein will now be described by way of example only and with reference to the accompanying drawings, in which.

Like reference numerals are used for like components where appropriate in the Figures.

DETAILED DESCRIPTION

Figure 1:
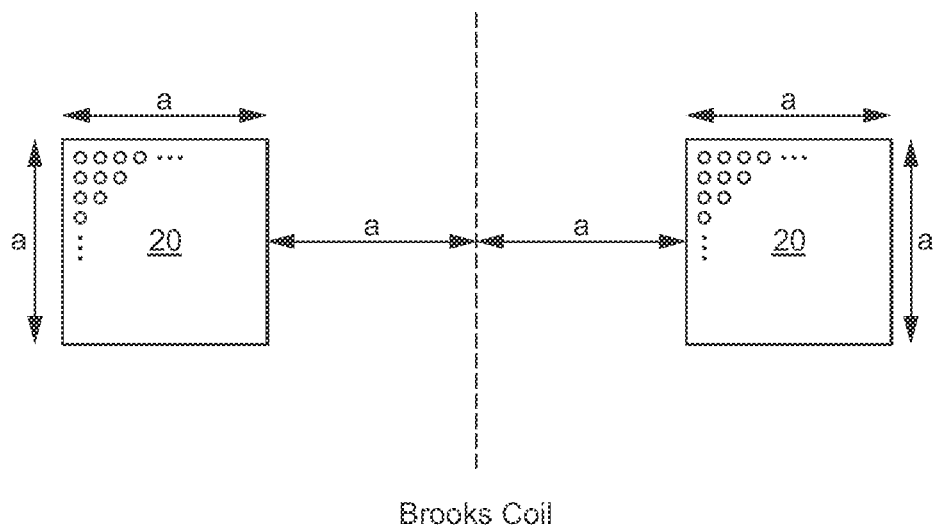
FIG. 1 shows the coil configuration for a Brooks coil.

A first embodiment of the technology described herein comprises a magnetometer system for medical use, comprising:

one or more induction coils for detecting a time varying magnetic field, each coil having a maximum outer diameter of 4 to 7 cm, and a configuration such that the ratio of the coil's length to its outer diameter is at least 0.5, and the ratio of the coil's inner diameter to its outer diameter is 0.5 or less; and a detection circuit coupled to each coil and configured to convert a current or voltage generated in the coil by a time varying magnetic field to an output signal for use to analyse the time varying magnetic field.

A second embodiment of the technology described herein comprises a method of analysing the magnetic field of a region of a subject's body, the method comprising:

using one or more induction coils to detect the time varying magnetic field of a region of a subject's body, each coil having a maximum outer diameter of 4 to 7 cm, and a configuration such that the ratio of the coil's length to its outer diameter is at least 0.5, and the ratio of the coil's inner diameter to its outer diameter is 0.5 or less;

converting a current or voltage generated in each coil by the time varying magnetic field of the region of a subject's body to an output signal; and using the output signal or signals from the coil or coils to analyse the magnetic field generated by the region of a subject's body.

A third embodiment of the technology described herein comprises a coil for use to detect the time-varying magnetic field of a region of a subject's body, the coil comprising:

an induction coil having a maximum outer diameter of 4 to 7 cm, and a configuration such that the ratio of the coil's length to its outer diameter is at least 0.5, and the ratio of the coil's inner diameter to its outer diameter is 0.5 or less.

The technology described herein provides a method and apparatus for detecting and analysing magnetic fields that are medically useful, such as the magnetic field of a region of a subject's body (for example of a subject's heart). However, in contrast to existing medical (e.g. cardiac) magnetometer designs, the technology described herein uses an induction coil or coils (i.e. a coil that is joined to an amplifier at both ends) of a specific configuration to detect the magnetic field of the subject (e.g. of the subject's heart). As will be discussed further below, the Applicants have found that induction coils having the particular configuration of the technology described herein can be used to provide a medical magnetometer that can be portable, relatively inexpensive, usable at room temperature and without the need for magnetic shielding, and yet can still provide sufficient sensitivity, accuracy and resolution to be medically useful.

The configuration of the induction coil of the technology described herein provides a number of advantages. Firstly, by limiting the outer diameter of the coil to 7 cm or less, a coil having an overall size that can achieve a spatial resolution that is suitable for medical magnetometry (and in particular for magneto-cardiography) is provided.

Setting the ratio of the coil's length to its outer diameter to at least 0.5 effectively means that the coil is relatively long for its width compared to a Brooks coil configuration, for example (for a Brooks coil this ratio is 0.25). Similarly, setting the ratio of the coil's inner diameter to its outer diameter to 0.5 or less effectively increases the number of windings for a given outer diameter compared to a Brooks coil configuration, for example (for a Brooks coil this ratio is 0.5).

The combination of these two requirements for the induction coil's configuration has firstly been found by the Applicants to make the coil of the technology described herein relatively more sensitive to magnetic field components along the axis of the coil. This provides two benefits. Firstly, it results in a higher output voltage from the coil for a given axial magnetic component. Secondly, it helps the spatial resolution of the coil as the coil is relatively more sensitive to components extending vertically through the centre of the coil when it is placed over a subject's body (e.g. over a subject's chest), and thus can provide a directional pick-up. Furthermore, the Applicants have recognised that it is the vertical components of the magnetic field generated by a region of a subject's body (e.g. by a subject's heart) that it is of particular interest to detect.

Thus the coil configuration of the technology described herein can provide an increase in the output voltage generated by the coil for the magnetic field components of interest. Moreover, the Applicants have found that this can be achieved without adversely affecting (and indeed even with reducing) the signal to noise ratio.

Indeed, the Applicants have found that the coil design of the technology described herein can provide a factor of 3 increase in the output voltage for a given axial magnetic component compared to a Brooks coil having the same outer diameter and a reduction of a factor of 2 in the signal to noise ratio.

Although these gains on their face may seem relatively small, the Applicants have recognised that they can have a significant effect on the usability (or otherwise) of the coil for medical magnetometry, e.g. for magnetocardiography. For example, reducing the signal to noise ratio by a factor of two, reduces the data collection time needed for a given analysis by a factor of four (e.g. from 2 hours to 30 minutes). Similarly, increasing the output voltage of the coil by a factor of 3 can reduce the data collection time needed by a factor of 9 for the same signal output (this is because digitising errors grow with smaller signals when the signal size is within an order of magnitude of the digitization step). Thus the overall impact of the gains provided by the coil configuration used in the technology described herein can be a factor of 36 in the data collection (scan) time. This can make all the difference between having a medically useful (and useable) magnetometer or not.

Accordingly the Applicants have found that the coil design of the technology described herein can provide an induction coil magnetometer that can perform sufficiently well for medical magnetometry, such as magnetocardiography, but without the drawbacks associated with a Brooks coil (or, indeed, SQUID magnetometers).

It should be noted here that the Applicants have achieved this not by following the conventional approach of attempting to optimise the inductance of the coil to optimise the signal detection strength (which would lead to a Brooke's coil configuration) but have instead sought to optimise the output voltage that the coil generates, whilst minimising the signal to noise ratio, whilst remaining within an overall size constraint that is suitable for medical magnetometry such as magnetocardiography. This results in a coil configuration that is a significant departure from a design that delivers the optimum inductance, and yet the Applicants have found that their coil design will provide a medically useful magnetometer, whereas a Brooks coil (i.e. a coil configured to maximise the inductance for a given length of wire) meeting the same overall size constraint will not.

The magnetometer system of the technology described herein can be used as a system and probe to detect any desired magnetic field produced by a subject (by the human (or animal) body). It is particularly suited to applications where it is desired to probe and measure relatively small magnetic fields with a spatial resolution of 2-3.5 cm, being half the diameter of the coils. It is in an embodiment used to detect (and analyse) the time-varying magnetic field of (or produced by) a region of the subject's body, such as their bladder, heart, head or brain, womb or a foetus. Thus it may be, and is in an embodiment, used to detect magnetic fields relating to the bladder, pregnancy, the brain, or the heart. In an embodiment, the magnetometer is used for (and configured for) one or more of: magnetocardiography, magnetoencephalography, analysis and detection of bladder conditions (e.g. overactive bladder), analysis and detection of foetal abnormalities, and detection and analysis of pre-term labour.

In an embodiment the magnetometer is used as a cardiac magnetometer and to detect and analyse the magnetic field of a subject's heart.

Thus, another embodiment of the technology described herein comprises a cardiac magnetometer system for analysing the magnetic field of a subject's heart, comprising:

one or more induction coils for detecting the time varying magnetic field of a subject's heart, each coil having a maximum outer diameter of 4 to 7 cm, and a configuration such that the ratio of the coil's length to its outer diameter is at least 0.5, and the ratio of the coil's inner diameter to its outer diameter is 0.5 or less; and a detection circuit coupled to each coil and configured to convert a current or voltage generated in the coil by the time varying magnetic field of a subject's heart to an output signal for use to analyse the magnetic field generated by the subject's heart.

Another embodiment of the technology described herein comprises a method of analysing the magnetic field of a subject's heart, the method comprising:

using one or more induction coils to detect the time varying magnetic field of a subject's heart, each coil having a maximum outer diameter of 4 to 7 cm, and a configuration such that the ratio of the coil's length to its outer diameter is at least 0.5, and the ratio of the coil's inner diameter to its outer diameter is 0.5 or less;

converting a current or voltage generated in each coil by the time varying magnetic field of the subject's heart to an output signal; and using the output signal or signals from the coil or coils to analyse the magnetic field generated by the subject's heart.

Another embodiment of the technology described herein comprises a coil for use to detect the time-varying magnetic field of a subject's heart, the coil comprising:

an induction coil having a maximum outer diameter of 4 to 7 cm, and a configuration such that the ratio of the coil's length to its outer diameter is at least 0.5, and the ratio of the coil's inner diameter to its outer diameter is 0.5 or less.

As will be appreciated by those skilled in the art, these embodiments of the technology described herein can and in an embodiment do include any one or more or all of the optional features described herein, as appropriate.

The magnetometer system of the technology described herein may comprise a single coil. In this case the coil will be moved over the subject (e.g. the subject's chest) to take readings from different positions in use, as is known in the art.

However, in one embodiment, the system comprises plural coils, e.g., and in an embodiment, 7-19, in an embodiment 16-19 coils.

Where the system comprises plural coils, some or all of the coils are in an embodiment arranged in a two-dimensional array. The coil array is in an embodiment configured such that when positioned appropriately over a subject (e.g. a subject's chest) the coil array can take readings from a suitable set of sampling positions without the need to further move the array over the subject. The array can otherwise have any desired configuration, such as being a regular or irregular array, a rectangular or circular array (e.g. formed of concentric circles), etc.

It would also be possible to have a three-dimensional arrangement of coils. In this case, there are in an embodiment plural, e.g. two, layers of coil arrays, one above the other, with each layer arranged as an array as discussed above for the two-dimensional array arrangement.

Each coil in an embodiment has a non-magnetically active core (i.e. the coil windings are wound around a non-magnetically active core), such as being air-cored. This helps to reduce the noise in use. However, magnetically active, such as ferrite or other magnetic material, cores may be used if desired.

Each coil has a maximum outer diameter of 4-7 cm. This facilitates a medically applicable diagnostic using 16 to 19 sampling positions (detection channels) to generate an image. (As discussed above, and as will be appreciated by those skilled in the art, the data for each sampling position can, e.g., be collected either by using an array of coils, or by using one (or several) coils that are moved around the chest to collect the data.) In an embodiment, coils of 7 cm diameter are used.

The or each coil is in an embodiment configured to be sensitive to signals between 1 Hz and 60 Hz, as this is the frequency range of the relevant magnetic signals of the heart. The coils are in an embodiment optimised for sensitivity to signals at around 30 Hz, as 30 Hz is the principle frequency component of a human heart beat.

The or each coil is in an embodiment sensitive to magnetic fields in the range 1-150 pT. The coils do not need to be sensitive in the fT range. The Applicants have found, contrary to the belief in the art that a cardiac magnetometer needs to have sensitivity in the fT range, that in fact pT sensitivity is adequate for cardiac (and other medically useful) magnetic field measurements.

As discussed above, the outer diameter, D, of the coil, the coil's inner diameter, Di, and the coil's length, l, are carefully selected in the technology described herein.

In an embodiment, the ratio of the coil's inner diameter to its outer diameter, Di:D, is less than 0.5:1. In an embodiment, the ratio of the coil's inner diameter to its outer diameter, Di:D, is also greater than or equal to 0.3:1. Thus, the ratio of the coil's inner diameter to its outer diameter, Di:D, is in an embodiment in the range 0.3:1 to 0.5:1, in an embodiment 0.3:1 to <0.5:1. In an embodiment it is substantially 0.425:1. These coil configurations have been found to give the lowest noise figure for the measurements of interest.

The ratio of the coil's length to its outer diameter, l:D, should be 0.5:1 or greater. It is in an embodiment not more than unity (1:1), in an embodiment in the range 0.5:1 to 0.8:1, and in an embodiment substantially 0.69:1. These configurations have been found to optimise the coil structure for measuring the axial component of the magnetic field (the component along the axis of the coil).

Thus, in an embodiment, the or each coil has the following configuration:

$$4\,\text{cm} \leq D \leq 7\,\text{cm}$$

$$\frac{l}{D} = 0.69 \text{ and } \frac{Di}{D} = 0.425$$

where:
D is the outer diameter of the coil
l is length of the coil and
Di is the inner diameter of the coil.

The outer diameter D affects the signal noise floor. A larger outer diameter D gives a lower noise floor. An outer diameter D in the range 4 cm≤D≤7 cm (and with its other parameters as set out above) gives a noise floor between 0.8 pT to 0.2 pT.

The number of turns on the coil will be determined by the wire radius and the coil length l. The wire radius can be selected as desired to determine the voltage output: a smaller wire radius will increase the voltage output but at the expense of increased coil resistance. In an embodiment, the wire radius is 0.2 mm to 1 mm, in an embodiment 0.5 mm. Any suitable conductor can be used for the wire.

In an embodiment, the number of windings for the or each coil is 1000 to 8000, in an embodiment 2000. The winding density (the ratio of the cross-sectional area of the winding to the cross-sectional area of the wire) is in an embodiment in the range 0.5 to 1, in an embodiment 1. It should be noted here that such winding densities are contrary to the assumption that lower winding densities would be preferable (as they should lead to a lower noise floor). The Applicants have recognised that reducing the winding density reduces the strength of the signal from the coil and in fact it is more beneficial to maintain a higher signal strength, even at the expense of a higher noise floor.

The detection circuit that a coil is coupled to and that is used to detect the output from the coil should, as discussed above, generate an appropriate output signal for analysis from the voltage and/or current that is induced in the coil by the magnetic field. Any suitable detection circuit and arrangement that can do this can be used. In an embodiment the detection circuit converts the voltage or current generated in the coil by the magnetic field into a digital signal for post-processing and averaging.

Where the system includes plural coils, each coil in an embodiment has its own, respective and separate, detection circuit (i.e. there will be as many detection circuits as there are coils). The output signals from the detection circuits can then be combined as desired in post-processing.

In an embodiment, each detection circuit operates in either a voltage or current sensing mode (in other words, detects and measures a signal generated between the ends of the coil by a time varying magnetic field), in an embodiment using a low noise amplifier.

Each detection circuit in an embodiment uses (includes) a detection amplifier, in an embodiment in the form of a microphone amplifier (a low impedance amplifier), connected to the ends of the coil.

In an embodiment the voltages produced by the detection circuit are digitised for post processing, noise reduction and signal recovery. In an embodiment the output voltage is digitised as early as possible (practical) in the detection setup to limit amplifier noise.

In an embodiment, one or more steps are taken to eliminate and/or compensate for any background magnetic field interference that may exist. Any suitable such techniques may be used, although it should be noted here that the technology described herein does not require the use of a magnetically shielded environment (and, indeed, the recognition that a shielded environment is not necessary is part of the inventive concept of the technology described herein and is an important advantage of the technology described herein).

In an embodiment, the mains (line) frequency (50 Hz in the UK) is removed from the output signal, in an embodiment by using an appropriate filter, such as and in an embodiment a notch filter, on the output signal. The Applicants have found that using a filter tuned to the line frequency is sufficient to eliminate most noise from the output signal. In an embodiment, a low pass filter with an appropriate cut-off frequency (e.g. 40 Hz, where the line frequency is 50 Hz) is used additionally to (try to) remove any remaining high frequency noise.

The Applicants have found that, particularly if the line frequency noise is removed, suitable output signals can be obtained without, e.g. the need for magnetic shielding or closely match gradiometer coils.

Thus, in an embodiment, the method of the technology described herein further comprises removing the mains (line) frequency from the output voltage, in an embodiment by applying an appropriate filter, in an embodiment a notch filter, to the output signal. In an embodiment the output signal for analysis is also low-pass filtered to try to remove any remaining high frequency noise.

Similarly, the or each detection circuit of the magnetometer system of the technology described herein in an embodiment further comprises an appropriate filter, such as and in an embodiment a notch filter, set to the mains (line) frequency that acts on the output signal from the coil, in an embodiment together with a further low pass filter that acts on the output signal of the mains (line) frequency filter.

In an embodiment, the (or each) detection circuit comprises a low impedance amplifier connected to the ends of the coil, which amplifier is then connected to a low pass filter, e.g. with a frequency cut-off of 250 Hz, a notch filter to remove line noise (e.g. 50 Hz), and, optionally, to an averaging element (which could be triggered in the cardio-magnetometry case, e.g., by a biological signal that is correlated to the heartbeat, e.g. via Pulse-Ox or an ECG). The detection circuit may be coupled to an appropriate signal analysis unit for analysing and signal processing the output signal produced by the detection circuit.

In an embodiment, the coil and detection circuit are arranged such that the coil and amplifier (that is coupled to the coil) of the detection circuit are arranged together in a sensor head or probe which is then joined by a wire to the remaining components of the detection circuit to allow the sensor head (probe) to be spaced from the remainder of the detection circuit in use.

Other or further techniques to try to eliminate or compensate for the effects of background noise can be used if desired. One suitable such technique is background field subtraction using a background field-only pick up coil (i.e. a coil that is not sensitive to the local field of the subject), in an embodiment in conjunction with appropriate coil matching (active or passive). The background field-only pick up coil(s) should be, and in an embodiment are, configured the same as the coil(s) that are being used to detect the "wanted" signal (the signal of interest) and coupled to corresponding detection circuits.

Thus in an embodiment, the apparatus and method of the technology described herein uses background noise pickup subtraction, in an embodiment with coil matching, to try to account for (and compensate for) the presence of background magnetic fields.

In this case, where the system uses plural coils, one or more of the coils could be used as background-pickup coils (i.e. to detect the background magnetic field, rather than the subject's heart's magnetic field). In this case, where there is an array of coils, one or more of the outer coils (e.g.) could be used to detect the background magnetic field, and/or if two or more layers of coil arrays are provided, one of the layers (or certain coils in one of the layers) could be used to detect the background magnetic field. Thus in an embodiment, the system comprises an array of plural coils, and one or more of the coils are used to detect the background magnetic field, with the remaining coils being used to detect the magnetic field of interest (e.g. the subject's heart's magnetic field).

In one embodiment, coil output signal matching is achieved by using two coils and adding a global field to both coils and then using lock-in amplification of the difference signal and feedback to an amplifier which controls the gain of one of the coils. This facilitates precision matching of the coils without the need for precision manufacturing of the coils (which can be very difficult and expensive). The frequency of the global modulation field is in an embodiment significantly higher than the frequency that is needed for medical detection (10-60 Hz), so as to move the frequency for lock-in detection well above the frequency that is needed for medical detection. In an embodiment the global modulation field has a frequency of at least 1 kHz.

A further advantage of using such a global modulation field coil matching technique is that it can then be used to subtract all global interfering (noise) fields, not just the mains (line) noise.

It should be noted that the Applicants have found that heart beat scale sensitivity can be achieved with the technology described herein without using gradient or background noise subtraction (or any equivalent process to compensate for background noise), although using gradient or background noise subtraction (or an equivalent process) will allow a useful signal to be produced more quickly.

The output signal(s) from the magnetometer (from each detection circuit) can be processed in any suitable and desired fashion. In an embodiment, the signal(s) are subjected to appropriate signal processing, for example to generate false colour images of the magnetic field.

In an embodiment, the signal over a number of heart beats is averaged to provide the output signal that will be used for any subsequent analysis and diagnosis. (The Applicants have found that sensitivity to a single heart beat is not necessary, as although the heart rate fluctuates a great deal over a short period of time, the actual shape of each pulse is very similar.)

In an embodiment a high data collection speed is maintained, and signal post-processing is used to generate the required signal, rather than using solutions such as slowing the response time of the detection circuit(s) to produce a valid signal.

In an embodiment, the analogue signal from each induction coil is digitised, and sorted into appropriate digital signal bins (and in an embodiment then averaged over a number of heart beats).

An ECG or Pulse-Ox trigger from the test subject may be used as a detection trigger for the signal acquisition process, but this is not absolutely necessary.

The system and method of the technology described herein can be used as desired to analyse the magnetic field, e.g. of the subject's heart. In an embodiment, suitable measurements are taken to allow an appropriate magnetic scan image of the heart (or other body region of interest) to be generated, which image can then, e.g., be compared to reference images for diagnosis. The technology described herein can be used to carry out any known and suitable procedure for imaging the magnetic field of the heart.

In an embodiment 16 to 19 sampling positions (detection channels) are detected in order to generate the desired scan image.

The technology described herein accordingly extends to the use of the magnetometer system of the technology described herein for analysing, and in an embodiment for imaging, the magnetic field generated by a subject's heart (or other body region), and to a method of analysing, and in an embodiment of imaging, the magnetic field generated by a subject's heart (or other body region) comprising using the method or system of the technology described herein to analyse, and in an embodiment to image, the magnetic field generated by a subject's heart (or other region of the body).

The analysis, and in an embodiment the generated image, is in an embodiment used for diagnosis of (to diagnose) a medical condition, such as abnormality of the heart, etc.

Thus another embodiment of the technology described herein comprises a method of diagnosing a medical condition, comprising using one or more induction coils to detect the time varying magnetic field of a region of a subject's body, each coil having a maximum outer diameter of 4 to 7 cm, and a configuration such that the ratio of the coil's length to its outer diameter is at least 0.5, and the ratio of the coil's inner diameter to its outer diameter is 0.5 or less;

using a detection circuit or circuits coupled to the coil or coils to convert a current or voltage generated in each coil by the time varying magnetic field of the region of the subject's body to a respective output signal for the coil;

using the output signal or signals from the coil or coils to analyse the magnetic field generated by the region of the subject's body; and using the analysis of the magnetic field generated by the region of the subject's body to diagnose said medical condition.

In this embodiment of the technology described herein, the output signal or signals from the coil or coils are in an embodiment used to produce an image representative of the magnetic field generated by the region of the subject's body, and the method in an embodiment then comprises comparing the image obtained with a reference image or images to diagnose the medical condition. The medical condition is, as discussed above, in an embodiment one of: abnormality of the heart, a bladder condition, pre-term labour, foetal abnormalities or abnormality of the head or brain.

As will be appreciated by those skilled in the art, these embodiments of the technology described herein can and in an embodiment do include any one or more or all of the optional features described herein, as appropriate.

As will be appreciated from the above, a particular advantage of the technology described herein is that it can be used in the normal hospital or surgery or other environment, without the need for magnetic shielding. Thus, in an embodiment, the methods of the technology described herein comprise using the magnetometer system to detect the magnetic field of a subject's heart (or other body region) in a non-magnetically shielded environment (and without the use of magnetic shielding).

As will be appreciated by those skilled in the art, all of the embodiments of the technology described herein can and in embodiments do include any one or more or all of the optional features described herein, as appropriate.

The methods in accordance with the technology described herein may be implemented at least partially using software e.g. computer programs. It will thus be seen that when viewed from further embodiments the technology described herein provides computer software specifically adapted to carry out the methods herein described when installed on data processing means, a computer program element comprising computer software code portions for performing the methods herein described when the program element is run on data processing means, and a computer program comprising code means adapted to perform all the steps of a method or of the methods herein described when the program is run on a data processing system. The data processing system may be a microprocessor, a programmable FPGA (Field Programmable Gate Array), etc.

The technology described herein also extends to a computer software carrier comprising such software which when used to operate a magnetometer system comprising data processing means causes in conjunction with said data processing means said system to carry out the steps of the methods of the technology described herein. Such a computer software carrier could be a physical storage medium such as a ROM chip, CD ROM or disk, or could be a signal such as an electronic signal over wires, an optical signal or a radio signal such as to a satellite or the like.

It will further be appreciated that not all steps of the methods of the technology described herein need be carried out by computer software and thus from a further broad embodiment the technology described herein provides computer software and such software installed on a computer software carrier for carrying out at least one of the steps of the methods set out herein.

The technology described herein may accordingly suitably be embodied as a computer program product for use with a computer system. Such an implementation may comprise a series of computer readable instructions either fixed on a tangible medium, such as a non-transitory computer readable medium, for example, diskette, CD ROM, ROM, or hard disk. It could also comprise a series of computer readable instructions transmittable to a computer system, via a modem or other interface device, over either a tangible medium, including but not limited to optical or analogue communications lines, or intangibly using wireless techniques, including but not limited to microwave, infrared or other transmission techniques. The series of computer readable instructions embodies all or part of the functionality previously described herein.

Those skilled in the art will appreciate that such computer readable instructions can be written in a number of programming languages for use with many computer architectures or operating systems. Further, such instructions may be stored using any memory technology, present or future, including but not limited to, semiconductor, magnetic, or optical, or transmitted using any communications technology, present or future, including but not limited to optical, infrared, or microwave. It is contemplated that such a computer program product may be distributed as a removable medium with accompanying printed or electronic documentation, for example, shrink wrapped software, pre loaded with a computer system, for example, on a system ROM or fixed disk, or distributed from a server or electronic bulletin board over a network, for example, the Internet or World Wide Web.

Figure 3:
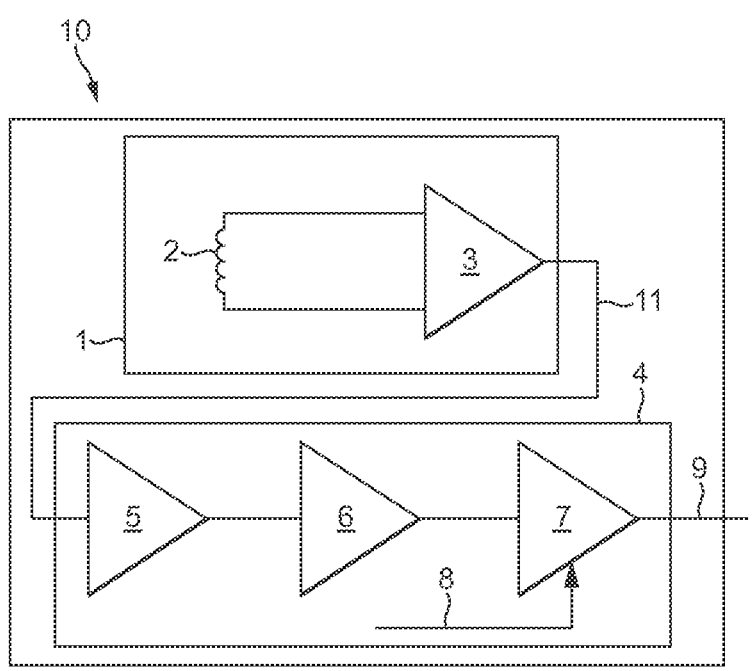
FIG. 3 shows schematically the basic construction of an embodiment of a magnetometer arrangement that is in accordance with the technology described herein.

FIG. 3 shows schematically the basic construction of an embodiment of a magnetometer system 10 that is in accordance with the technology described herein. This magnetometer system 10 is specifically intended for use as a cardiac magnetometer (for use to detect the magnetic field of a subject's heart). However, as discussed above, the same magnetometer design can be used to detect the magnetic field produced by other body regions, for example for detecting and diagnosing bladder conditions, pre-term labour, foetal abnormalities and for magnetoencephalography. Thus, although the present embodiment is described with particular reference to cardio-magnetometry, it should be noted that the present embodiment (and the technology described herein) extends to other medical uses as well.

The magnetometer 10 comprises a coil 2 coupled to a detection circuit that contains a number of components.

The coil 2 is an induction coil 2 having, e.g., 6000 windings, and a configuration that is in accordance with the technology described herein. The coil 2 is coupled to a detection circuit comprising firstly a low impedance preamplifier 3, such as a microphone amplifier, that is connected to the coil 2.

The preamplifier 3 is then connected by a wire 11 to the rest of the detection circuit which comprises a low pass filter 5, e.g. with a frequency cut-off of 250 Hz, a notch filter 6 to remove line noise (e.g. 50 Hz), and an averaging element 7 (this is optional) which could be triggered 8 by a biological signal that is correlated to the heartbeat, e.g. via Pulse-Ox or an ECG. The detection circuit produces an output signal 9 for analysis. The detection circuit may be coupled to an appropriate signal analysis unit for analysing and signal processing the output signal, Vout 9.

As shown in FIG. 3, the coil and detection circuit are arranged such that the coil 2 and the preamplifier 3 of the detection circuit are arranged together in a sensor head or probe 1 which is then joined by a wire 11 to a processing circuit 4 that comprises the remaining components of the detection circuit. Connecting the sensor head (probe) 1 and the processing circuit 4 by wire allows the processing circuit 4 to be spaced from the sensor head (probe) 1 in use.

With this magnetometer, the sensor head (probe) 1 will be used as a magnetic probe by placing it in the vicinity of the magnetic fields of interest.

The detection circuit shown in FIG. 3 has been found to be robust to small magnetic signals, to have a high amplification factor and to be highly sensitive to the coil's output voltage. The Applicants have determined that, in a normal laboratory situation with no shielding, the only noise source interfering with the signal is line noise, so a high quality factor (narrow band) notch filter 6 tuned to the line frequency (e.g. 50 Hz) is sufficient to eliminate most noise. Any remaining high frequency noise can be removed with a low pass filter 5 with an appropriate cut-off frequency, if desired.

The design of the induction coil 2 for use in embodiments of the technology described herein will now be described. As discussed above, the coil should be a coil that is sufficiently sensitive to be able to detect the time-varying magnetic field of a subject's heart, but also have an overall size that permits spatial resolution suitable for magneto-cardiography.

The coil 2 in the present embodiments is air-cored (i.e. the coil windings are wound around a non-magnetically active core). However other arrangements, such as a ferrite or other magnetic material core may be used if desired (although the Applicants have found that such cores can increase the noise and hence the time needed to achieve a suitable diagnostic signal).

The frequency of the relevant magnetic signals of the heart is between 1 Hz and 60 Hz. Thus, the coil of the present embodiments is designed to be sensitive to magnetic fields at these frequencies.

The Applicants have recognised that at these frequencies the coil design of the technology described herein will have an output voltage determined by $$V = AN\frac{dB(t)}{dt} = ANB2\pi f \quad (1)$$

where N is the number of windings, A is the effective cross sectional area of the coil, B(t) is the time varying magnetic field with a magnitude B, and f is the frequency of oscillation of the field.

If B is set to 1 pT (i.e. B=1 pT), which the Applicants have recognised is the smallest field it is necessary and desirable to be able to measure accurately for cardiac measurements, and f is set to 30 Hz (i.e. f=30 Hz) (which is the main frequency of interest for cardiac measurements) in the above equation, the conversion rate (output voltage) for the signal frequencies that are of the greatest interest for the coil design can be determined.

Furthermore, the smallest field that can be detected given thermal noise resulting from the winding resistance is given by:

$$S = \frac{\sqrt{4k_B T R_a}}{2\pi f N A} \quad (2)$$

where $k_B$ is Boltzmans constant, T is the temperature, and $R_a$ is the antenna wire resistance, which is given by:

$$R_a = N 2\pi^2 a^2 \rho r_{coil} \quad (3)$$

where a is the radius and ρ is the resistivity of the wire used in the windings on a circular coil of average winding radius $r_{coil}$.

Figure 2:
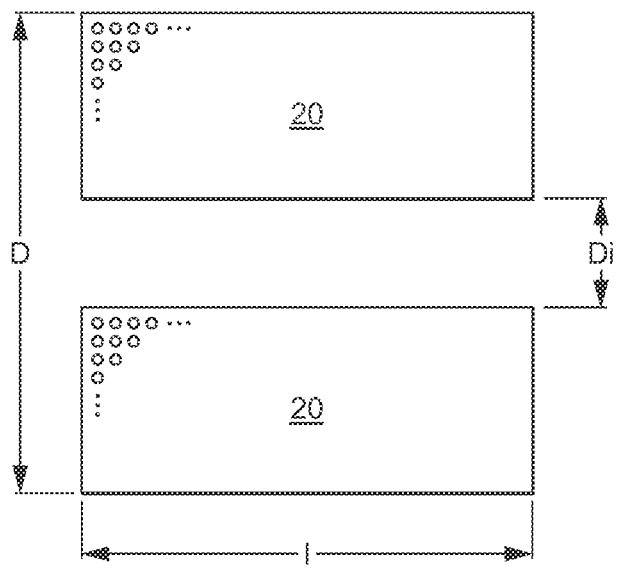
FIG. 2 shows the coil configuration for a magnetometer that is in accordance with the technology described herein.

If coil parameters of the length l, outer diameter D and inner diameter Di of the coil, as illustrated in FIG. 2, are defined, then using equations (1)-(3) above a suitable (and the optimum) coil structure can be determined. (In FIG. 2 the boxes 20 represent the winding area.)

Following this approach, the Applicants have found that the coil structure that gives the lowest noise figures for the frequencies of interest has a ratio of inner to outer diameter, Di:D, in the range 0.3 to 0.5, in an embodiment 0.3 to <0.5, and in an embodiment Di:D≈0.425.

Furthermore, the optimum coil structure to measure the axial component of the magnetic field (along the axis of the coil), which is the component of interest, is achieved when l/D≥0.5, in an embodiment 0.5-1, more in an embodiment 0.5-0.8, and in an embodiment≈0.69 (when Di/D≈0.425).

In an embodiment, the maximum diameter D of the coil is around 7 cm. This is based on a maximum size of coil that will be suitable for a medically applicable diagnostic, assuming that the minimum number of sampling positions (detection channels) that is required for a medically useful image is sixteen to nineteen (which is the minimum number of sampling positions (channels) usually required for a valid diagnostic, depending on the assembly of the imaging system).

Thus, the present embodiment of the technology described herein uses an induction coil 2 having the following structure:

$$4 \leq D \leq 7 \text{ cm}$$

$$\frac{l}{D} = 0.69 \text{ and } \frac{Di}{D} = 0.425$$

where:
D is the outer diameter of the coil
l is length of the coil and
Di is the inner diameter of the coil.

The number of turns on the coil is determined by the wire radius a and the coil length l. The wire radius may be selected as desired to determine the voltage output: a smaller wire increases the voltage output at the expense of increased coil resistance.

The table below compares the performance of coils having the above configuration with the performance of a Brooks coil having the same outside dimension at the target frequency of 30 Hz (and using the detection circuit of FIG. 3). (The Brooks coil design has been chosen as a comparator, as the normal mode of thinking is to optimise the coil inductance. For any given length of wire, the coil with the highest inductance is given by the Brooks configuration.)

|  | Coil Outer Diameter D | Coil Inner Diameter Di | Coil Length l | Wire radius a | Output voltage for 1 pT field | Sensitivity S (smallest field that can be detected) |
|---|---|---|---|---|---|---|
| Coil of the present embodiment | 12 cm | 5.1 cm | 8.28 cm | 0.23 mm | 616 nV | 57 fT |
| Brooks Coil | 12 cm | 6 cm | 3 cm | 0.23 mm | 211 nV | 96 fT |
| Coil of the present embodiment | 8.5 cm | 3.6 cm | 5.87 cm | 0.23 mm | 155 nV | 136 fT |
| Brooks Coil | 8.5 cm | 4.25 cm | 2.125 cm | 0.23 mm | 53 nV | 227 fT |
| Coil of the present embodiment | 4.25 cm | 1.8 cm | 2.9 cm | 0.23 mm | 9.5 nV | 773 fT |
| Brooks Coil | 4.25 cm | 2.125 cm | 1.0625 cm | 0.23 mm | 3.3 nV | 1.3 pT |

This table shows that the coil design of the present embodiments has significant improvements over a Brooks coil of the same outside dimension. The coil of the present embodiments has a higher voltage and lower noise figure at the target frequency of 30 Hz.

Figure 4:
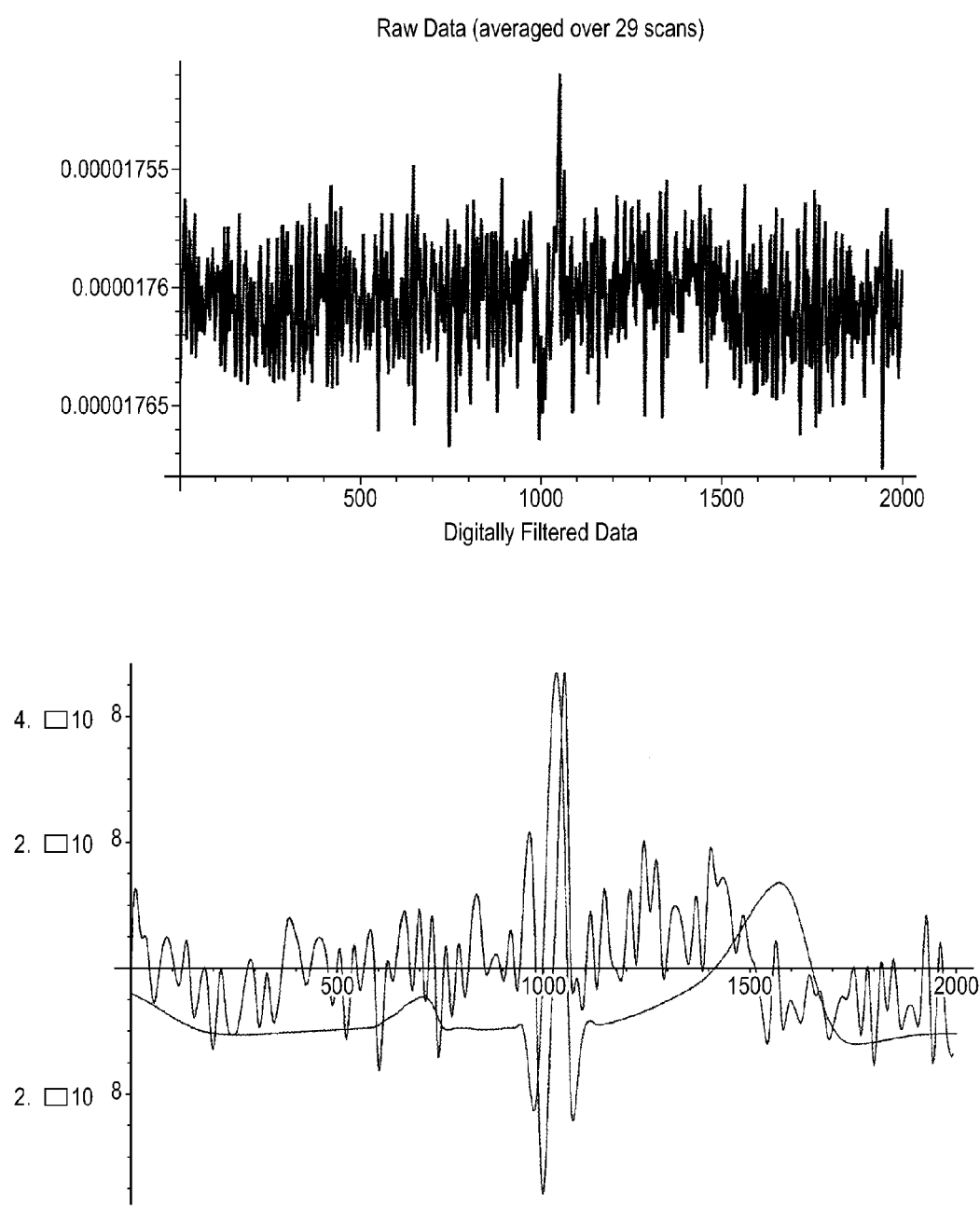
FIG. 4 shows an exemplary output obtained using the magnetometer arrangement of FIG. 3.

FIG. 4 shows an exemplary output obtained with the magnetometer system shown in FIG. 3.

FIGS. 5-13 show exemplary arrangements for using the coils and detection circuits of embodiments for detecting and imaging the magnetic field of the human heart.

Figure 5:
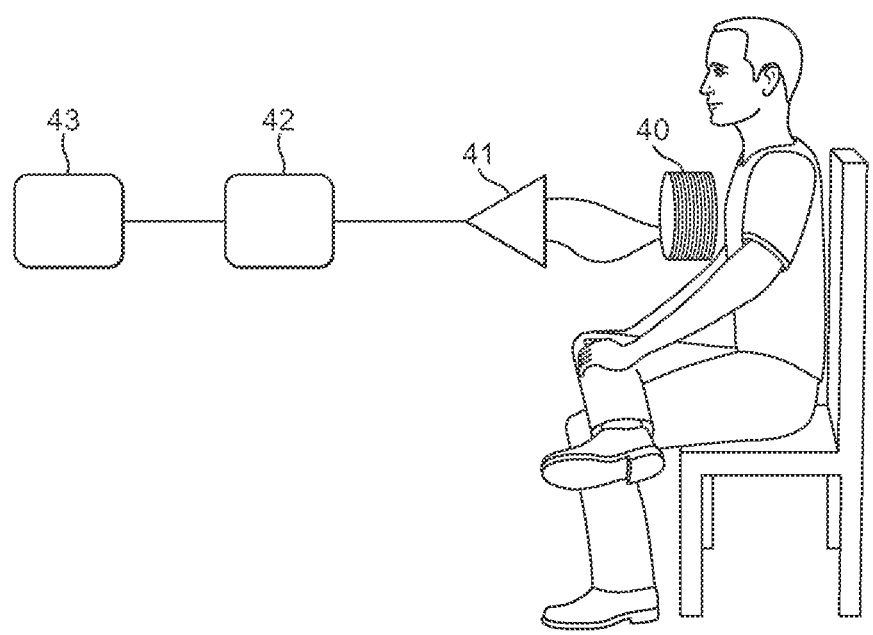
FIG. 5 shows schematically the use of an embodiment of the technology described herein for detecting the magnetic field of a subject's heart.

FIG. 5 shows the most basic mode of operation. In this case, the current output from a single coil 40 is processed and converted to a voltage by the detection circuit 41 and provided to an A/D converter 42 which digitalises the analogue signal from the coil 40 and provides it to a data acquisition system 43. An ECG or Pulse-Ox trigger from the test subject is used as a detection trigger for the digital signal acquisition (however, this is not necessary and so it can be omitted if desired), and the digitised signal over a number of trigger pulses is then binned into appropriate signal bins, and the signal bins overlaid or averaged, by the data acquisition unit 43.

Figure 6:
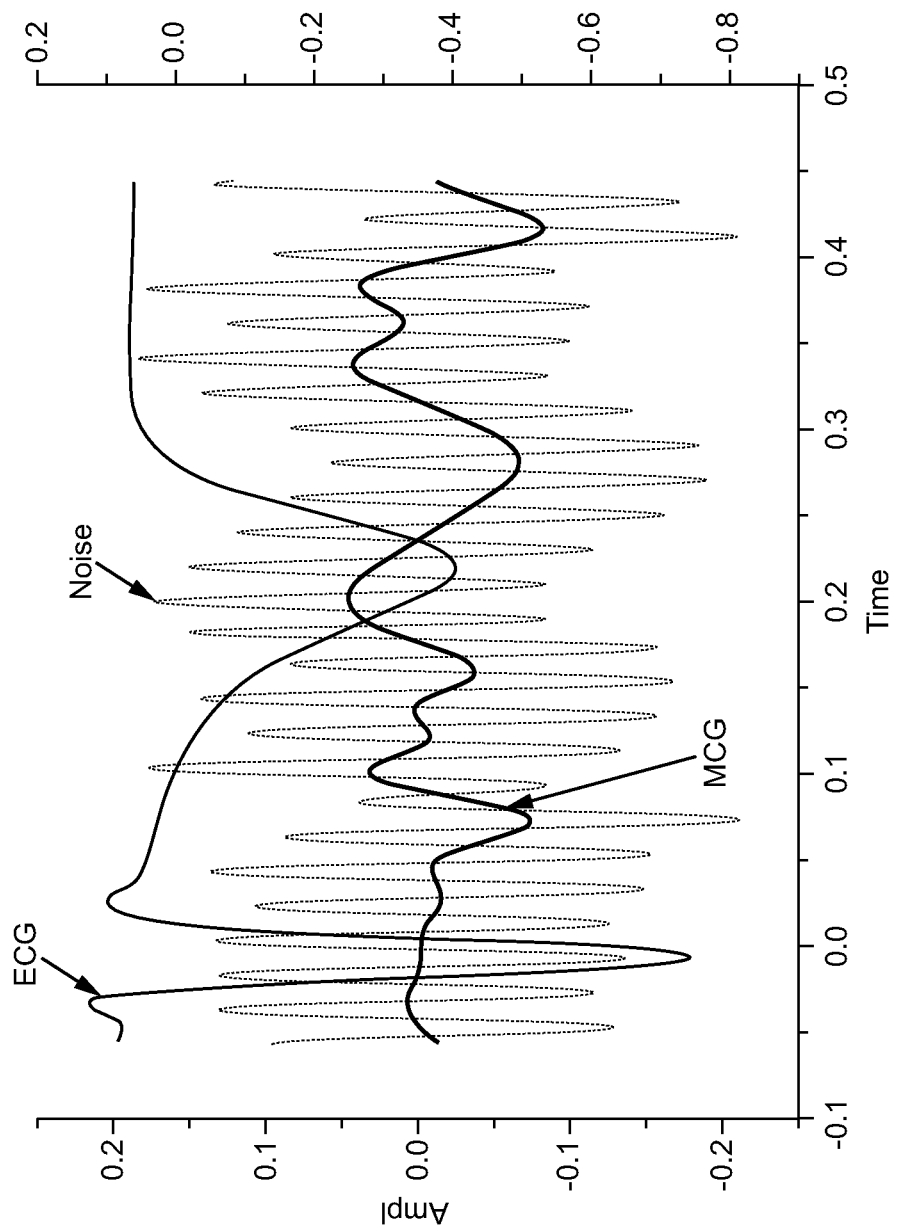
FIG. 6 shows an exemplary output obtained with the FIG. 5 arrangement.

FIG. 6 shows a set of exemplary results for this configuration. The signal, MCG, from the heart is clear, but because the signal detection is noisy, requires filtering and averaging of the detected signal to produce. However, the Applicants have found that this arrangement will work with a 4 cm diameter coil.

Figure 7:
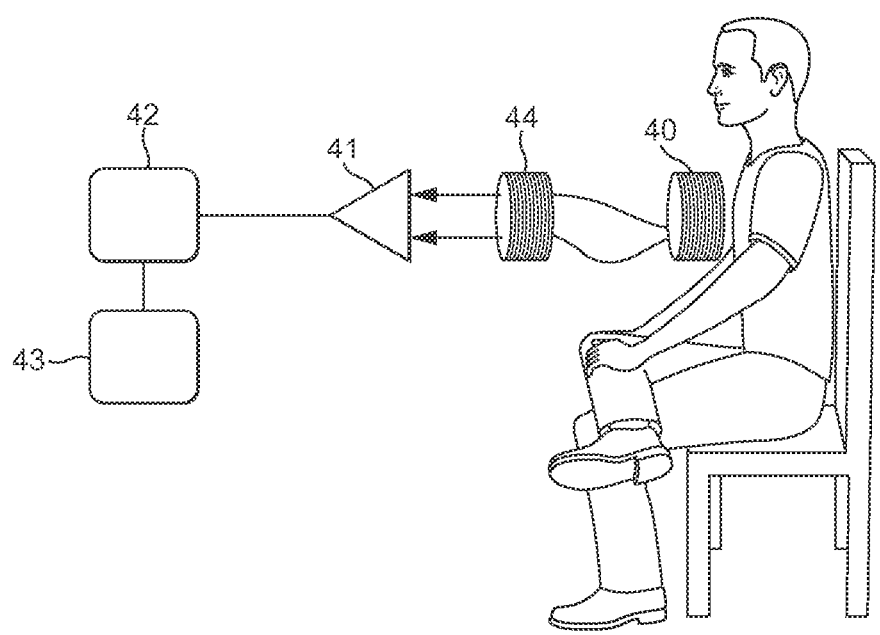
FIG. 7 shows a further exemplary arrangement of the use of an embodiment of the technology described herein when detecting the magnetic field of a subject's heart.

FIG. 7 shows an improvement over the FIG. 5 arrangement, which uses in particular the technique of gradient subtraction to try to compensate for background noise. In this case, an inverse coil 44 is used to attempt to subtract the effect of the background noise magnetic field from the signal detected by the probe coil 40. The inverse coil 44 will, as is known in the art, be equally sensitive to any background magnetic field, but only weakly sensitive to the subject's magnetic field. The inverse coil 44 can be accurately matched to the pick-up coil 40 by, for example, using a movable laminated core to tune the performance of the inverse coil to that of the pick-up coil 40.

Figure 8A:
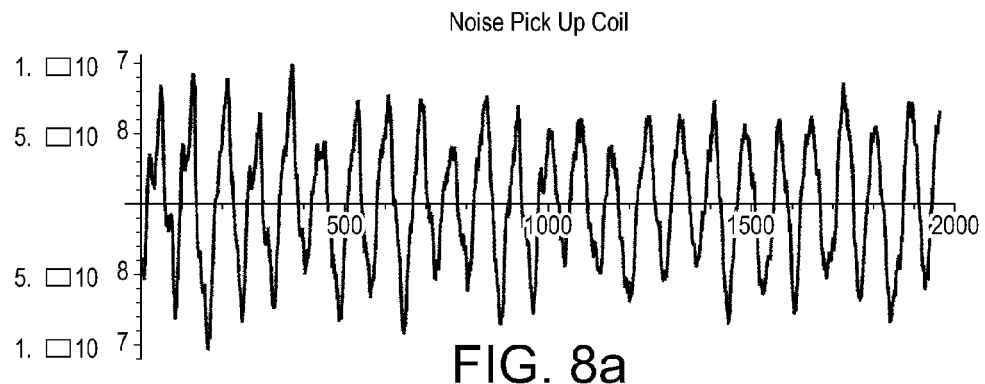
FIG. 8 shows exemplary results obtained using the arrangement of FIG. 7.
Figure 8B:
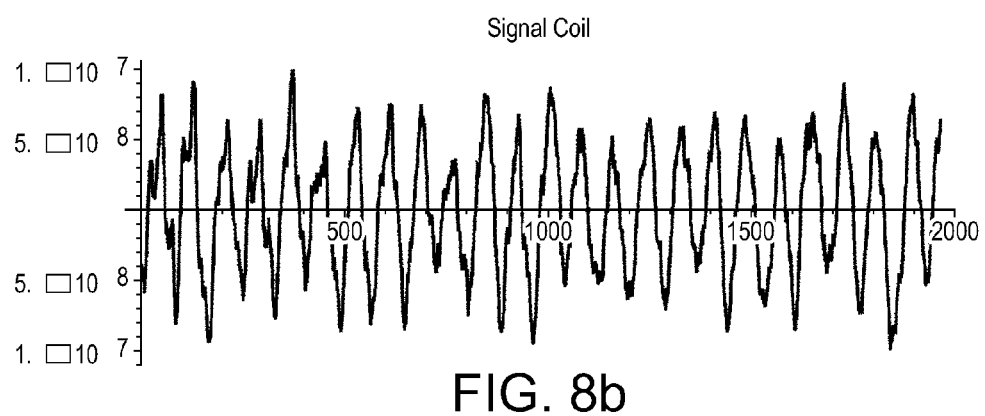
Figure 8C:
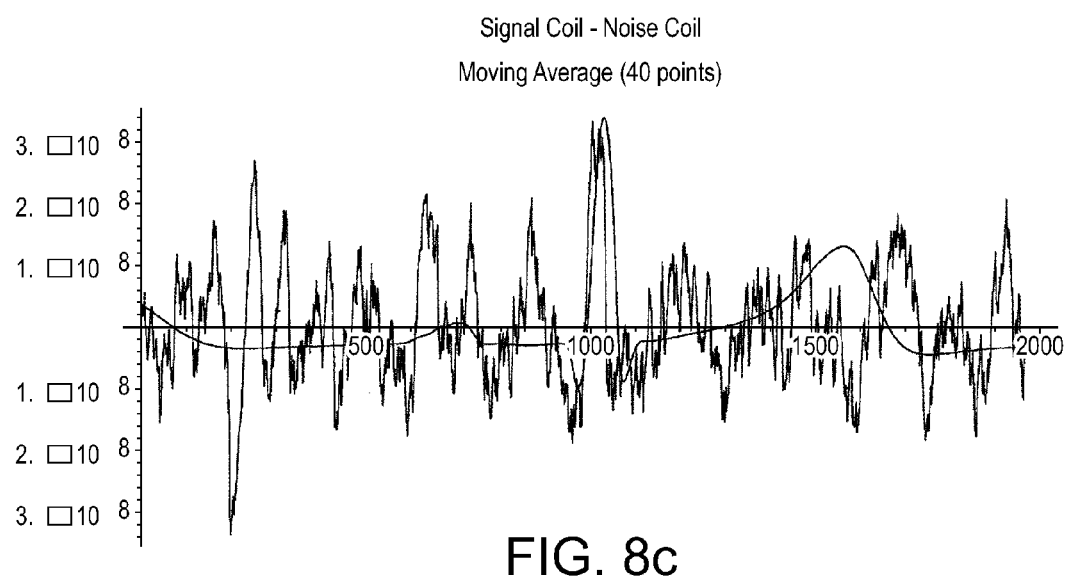

The Applicants have found that this technique again can provide a usable representation of the magnetic field of the heart using a 4 cm coil pair. FIG. 8 shows exemplary results for this arrangement. FIG. 8a shows the background noise signal detected by the inverse coil 44, FIG. 8b shows the "wanted" signal detected by the probe coil 40, and FIG. 8c shows the result of subtracting the "noise" signal from the "wanted" signal. In this case, passive signal filtering was used to post-process the magnetic, MCG, signal, but less post-processing than in the arrangement illustrated in FIGS. 5 and 6 is required.

Figure 9:
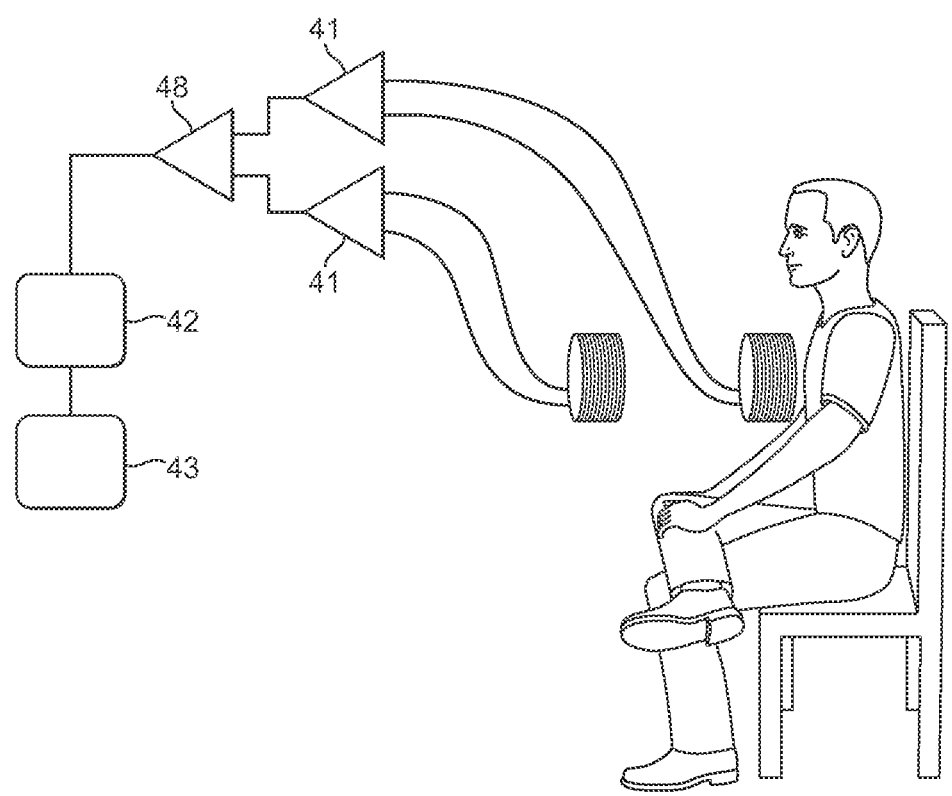
FIGS. 9, 10, 11, 12 and 13 show further exemplary arrangements for using embodiments of the technology described herein to detect the magnetic field of a subject's heart.

FIG. 9 shows an alternative gradient subtraction arrangement. In this case, both coils 40, 44 have the same orientation, but their respective signals are subtracted using a differential amplifier 45. Again, the best operation is achieved by accurately matching the coils and the performance of the detection circuits 41. Again, a movable laminated core can be used to tune the performance of one coil to match the performance of the other.

Figure 10:
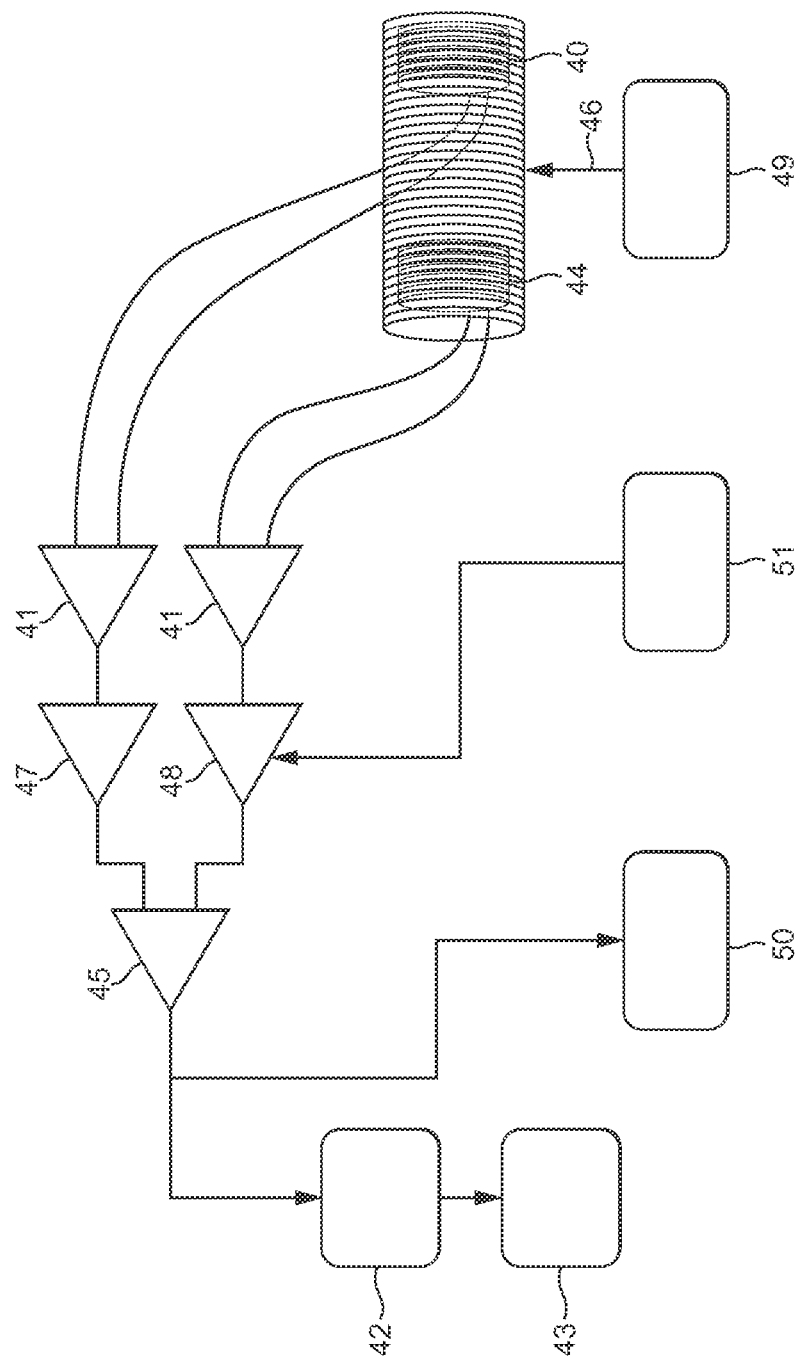

FIG. 10 shows a further embodiment. This circuit operates on the same principle as the arrangement of FIG. 9, but uses a more sophisticated method of field cancellation, and passive coil matching. In particular, a known global magnetic field 44 is introduced to both coils 40, 44 to try to remove background magnetic field interference.

In this circuit, the outputs from the detection circuits 41 are passed through respective amplifiers 47, 48, respectively, before being provided to the differential amplifier 45. At least one of the amplifiers 47, 48 is tunable. In use, a known global field 46, such as 50 Hz line noise, or a signal, such as a 1 kHz signal, applied by a signal generator 49, is introduced to both coils 40, 44. The presence of a signal on this frequency on the output of the differential amplifier 45, which can be observed, for example, using an oscilloscope 50, will then indicate that the coils 40, 44 are not matched. An amplifier control 51 can then be used to tune the tunable voltage controlled amplifier 48 to eliminate the global noise on the output of the differential amplifier 45 thereby matching the outputs from the two coils appropriately.

In an embodiment in this arrangement, a known global field of 1 kHz or so is applied to both coils, so as to achieve the appropriate coil matching for the gradient subtraction, but also a filter to remove 50 Hz noise is applied to the output signal.

Figure 11:
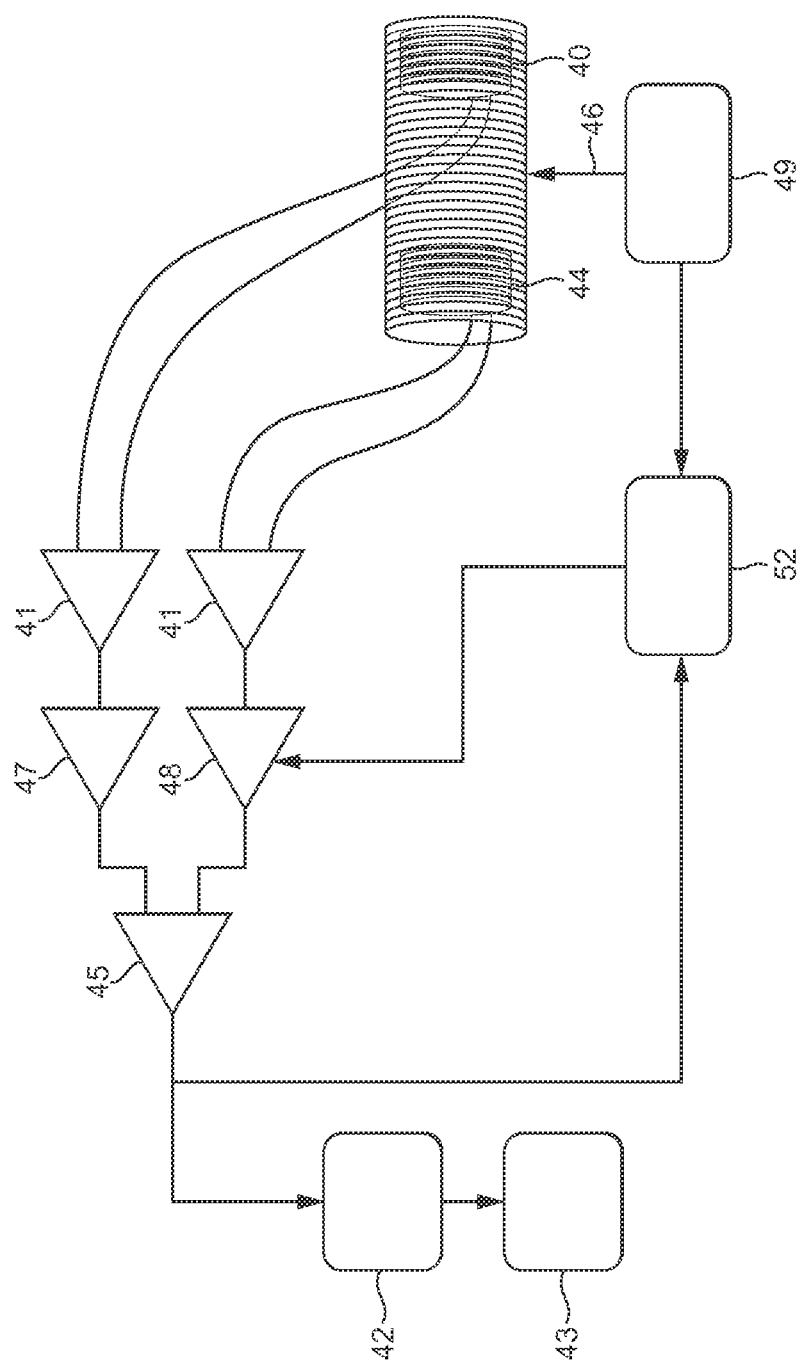

FIG. 11 shows a further variation on the FIG. 10 arrangement, but in this case using active coil matching. Thus, in this arrangement, the outputs of the coils 40, 44 are again channeled to appropriate detection circuits 41, and then to respective amplifiers 47, 48, at least one of which is tunable. However, the tunable amplifier 48 is tuned in this arrangement to remove the common mode noise using a lock-in amplifier 52 or similar voltage controller that is appropriately coupled to the output from the differential amplifier 45 and the signal generator 49.

The above embodiments of the technology described herein show arrangements in which there is a single pickup coil that may be used to detect the magnetic field of the subject's heart. In these arrangements, in order then to make a diagnostic scan of the magnetic fields generated by a subject's heart, the single pickup coil can be moved appropriately over the subject's chest to take readings at appropriate spatial positions over the subject's chest. The readings can then be collected and used to compile appropriate magnetic field scans of the subject's heart.

It would also be possible to arrange a plurality of coil and detection circuit arrangements, e.g. of the form shown in FIG. 3, in an array, and to then use such an array to take measurements of the magnetic field generated by a subject's heart. In this case, the array of coils could be used to take readings from plural positions over a subject's chest simultaneously, thereby, e.g., avoiding or reducing the need to take readings using the same coil at different positions over the subject's chest.

Figure 13:
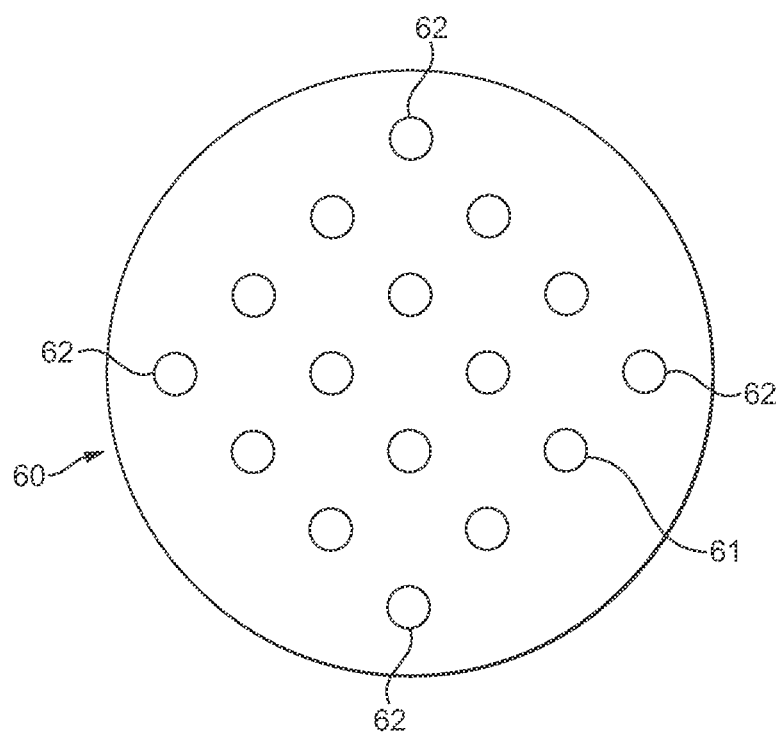

FIG. 13 shows a suitable coil array arrangement that has an array 60 of 16 detection coils 61, which may be then placed over a subject's chest to measure the magnetic field of a subject's heart at 16 sampling positions over the subject's chest. In this case, each coil 61 of the array 60 should be configured as described above and connected to its own respective detection circuit (i.e. each individual coil 61 will be arranged and have a detection circuit connected to it as shown in FIG. 3). The output signals from the respective coils 61 can then be combined and used appropriately to generate a magnetic scan of the subject's heart.

Other array arrangements could be used, if desired, such as circular arrays, irregular arrays, etc.

It would also be possible in this arrangement to use some of the coils 61 to detect the background magnetic field for the purposes of background noise subtraction, rather than for detecting the wanted field of the subject's heart. For example, the outer coils 62 of the array could be used as background field detectors, with the signals detected by those coils then being subtracted appropriately from the signals detected by the remaining coils of the array. Other arrangements for background noise subtraction would, of course, be possible.

It would also be possible to have multiple layers of arrays of the form shown in FIG. 13, if desired. In this case, there could, for example, be two such arrays, one on top of each other, with the array that is closer to the subject's chest being used to detect the magnetic field generated by the subject's heart, and the array that is further away being used for the purposes of background noise detection.

To measure the magnetic fields generated by the heart, the above arrangements can be used to compile magnetic field scans of a subject's heart by collecting magnetic field measurements at intervals over the subject's chest. False colour images, for example, can then be compiled for any section of the heart beat, and the scans then used, for example by comparison with known reference images, to diagnose various cardiac conditions. Moreover this can be done for significantly lower costs both in terms of installation and ongoing running costs, than existing cardiac magnetometry devices.

Figure 12:
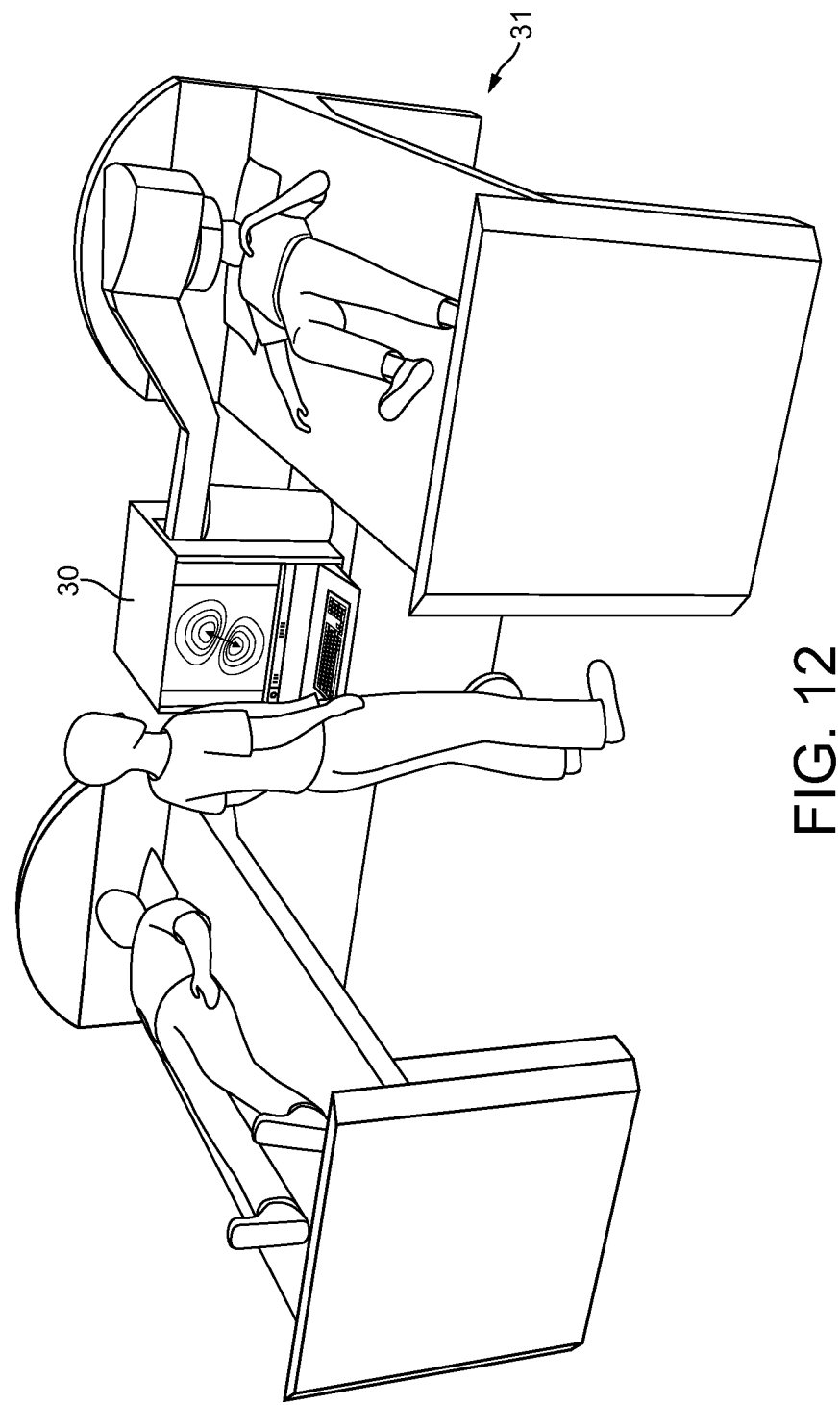

FIG. 12 shows an exemplary arrangement of the magnetometer as it is envisaged it may be used in a hospital, for example. The magnetometer 30 is a portable device that may be wheeled to a patient's bedside 31 where it is then used to take a scan of the patient's heart (e.g.). There is no need for any magnetic shielding, cryogenic cooling, etc. The magnetometer 30 can be used in the normal ward environment.

It should be noted here that the signal generated by the pick-up coil in the present embodiments will be the derivative of the useful signal, so the output signal can be (and in an embodiment is) integrated over time to generate the wanted, useful signal. Such integration will also have the effect of tending to remove the effect of noise from the signal (provided the noise amplitude is not too big). Furthermore, the noise will remain in the integrated signal and so can be recovered if desired or needed, by taking the derivative of the integrated signal.

Figure 14:
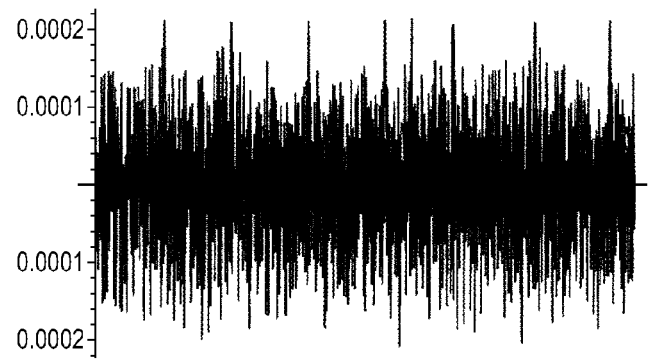
FIGS. 14 and 15 show further exemplary results obtained using cardiac magnetometers in accordance with the technology described herein.
Figure 14:
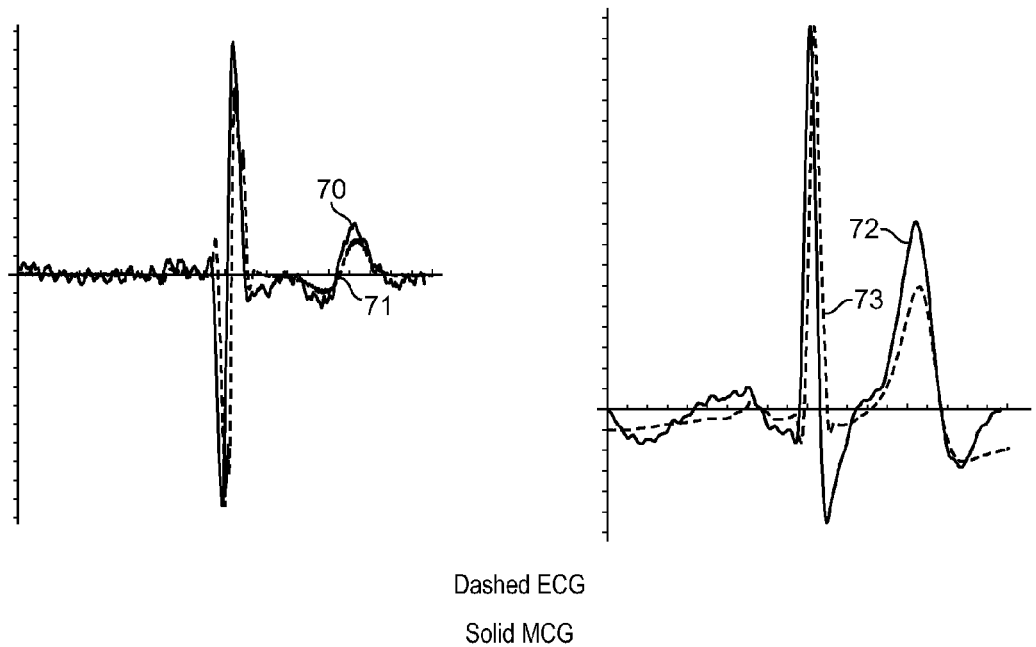
Figure 15:
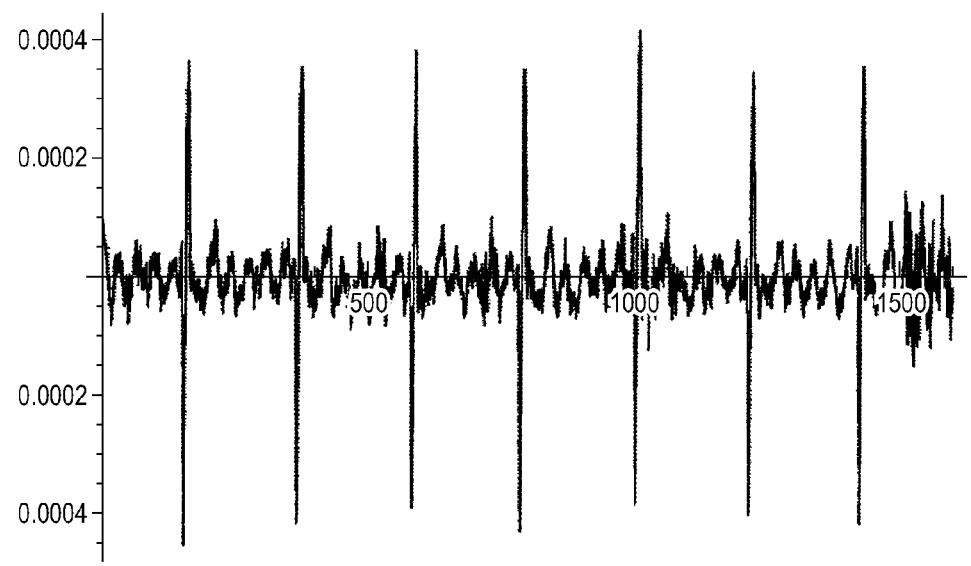
Figure 15:
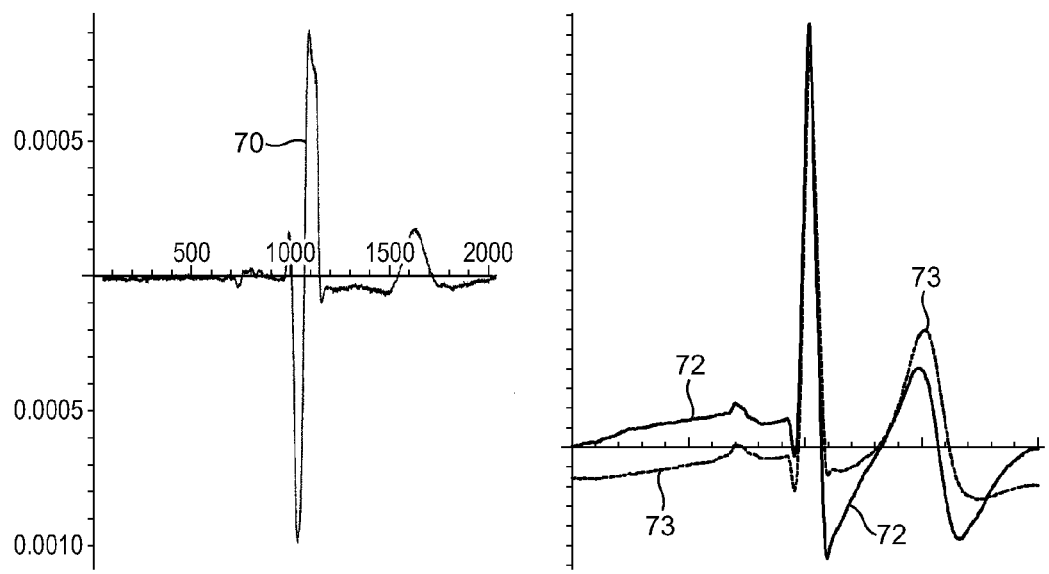

FIGS. 14 and 15 show further exemplary results obtained using the cardiac magnetometer of the present embodiments.

FIG. 14 shows exemplary results obtained from a 20 minute magnetocardiograph scan taken in an ordinary laboratory environment using a pick-up coil to provide background noise subtraction. The double coil configuration and system shown in FIG. 11 was used, with the signal detecting coil placed over the Xiphoid process and the second coil placed with its centre displaced by 8 cm higher on the chest and the same distance from the body.

FIG. 14 shows the raw trace, the averaged magnetic signal 70 (over the 20 minute scan) for a single heart beat against the corresponding differentiated ECG signal 71, and the integrated magnetic signal 72 against the ECG trace 73.

FIG. 15 shows the corresponding results obtained when using the same coil arrangement but in a magnetically shielded environment, and without using background noise subtraction. In this case the single coil was placed over the Xiphoid process. The results for a raw magnetocardiograph scan averaged over a period of 1 minute are shown.

The magnetometer system can be used in an analogous manner to detect and analyse other medically useful magnetic fields produced by other regions of the body, such as the bladder, head, brain, a foetus, etc.

It can be seen from the above that the technology described herein, in its embodiments at least, provides a magnetic imaging device that can be deployed effectively from both a medical and cost perspective in a wide range of clinical environments, e.g. for use when detecting magnetic fields generated by the heart. The magnetometer is, in particular, advantageous in terms of its cost, its practicality for use in clinical environments, and its ability to be rapidly deployed for near patient diagnosis and for a wide range of applications. It is non-contact, works through clothing, fast, compact and portable and affordable. An image can be recovered with high resolution after a minute of signal recording and absolute "single beat" sensitivity is potentially possible. Patient motion of up to 1-2 cm will not significantly degrade the image.

This is achieved, in embodiments of the technology described herein at least, by using an improved design of detection coil that is configured to detect the time-varying magnetic of the (e.g.) heart, using a detection circuit in a current or voltage sensing mode, and then processing the signals to remove common mode noise and using digital recording and signal averaging to analyse them.

The foregoing detailed description has been presented for the purposes of illustration and description. It is not intended to be exhaustive or to limit the technology to the precise form disclosed. Many modifications and variations are possible in the light of the above teaching. The described embodiments were chosen in order to best explain the principles of the technology and its practical application, to thereby enable others skilled in the art to best utilise the technology in various embodiments and with various modifications as are suited to the particular use contemplated. It is intended that the scope be defined by the claims appended hereto.

What is claimed is:

1. A magnetometer system for medical use, comprising:
   one or more induction coils for detecting a time varying magnetic field, each coil having a maximum outer diameter of 4 to 7 cm, and a configuration such that the ratio of the coil's length to its outer diameter is in the range 0.5:1 to 0.8:1, and the ratio of the coil's inner diameter to its outer diameter is in the range 0.3:1 to 0.5:1; and
   a detection circuit coupled to each coil and configured to convert a current or voltage generated in the coil by a time varying magnetic field to an output signal for use to analyse the time varying magnetic field.

2. The magnetometer system of claim 1, comprising plural induction coils arranged in a two-dimensional array.

3. The magnetometer system of claim 1, wherein the ratio of each coil's inner diameter to its outer diameter is 0.425:1 and the ratio of each coil's length to its outer diameter is 0.69:1.

4. The magnetometer system of claim 1, wherein the number of windings of each coil is 1000 to 8000, and the winding density of each coil is in the range 0.5 to 1.

5. The magnetometer system of claim 1, wherein each detection circuit comprises a low impedance amplifier connected to the ends of the coil.

6. The magnetometer system of claim 5, wherein the coil or coils and the respective low impedance amplifier or amplifiers of the detection circuit or circuits are arranged together in a sensor head which is then joined by a wire or wires to the remaining components of the detection circuit or circuits to allow the sensor head to be spaced from the remainder of the detection circuit or circuits in use.

7. The magnetometer system of claim 1, wherein the system uses plural induction coils, and one or more of the coils are to be used to detect the background magnetic field, rather than the magnetic field of interest.

8. A cardiac magnetometer system for analysing the magnetic field of a subject's heart, comprising the magnetometer system of claim 1.

9. A coil for use to detect the time-varying magnetic field of a region of a subject's body, the coil comprising:
   an induction coil having a maximum outer diameter of 4 to 7 cm, and a configuration such that the ratio of the coil's length to its outer diameter is in the range 0.5:1 to 0.8:1, and the ratio of the coil's inner diameter to its outer diameter is in the range 0.3:1 to 0.5:1.

10. A method of analysing the magnetic field of a region of a subject's body, the method comprising:
   using one or more induction coils to detect the time varying magnetic field of a region of a subject's body, each coil having a maximum outer diameter of 4 to 7 cm, and a configuration such that the ratio of the coil's length to its outer diameter is in the range 0.5:1 to 0.8:1, and the ratio of the coil's inner diameter to its outer diameter is in the range 0.3:1 to 0.5:1;
   using a detection circuit or circuits coupled to the coil or coils to convert a current or voltage generated in each coil by the time varying magnetic field of the region of the subject's body to a respective output signal for the coil; and
   using the output signal or signals from the coil or coils to analyse the magnetic field generated by the region of the subject's body.

11. The method of claim 10, comprising using the induction coils to detect the magnetic field of a region of a subject's body in a non-magnetically shielded environment.

12. The method of claim 10, comprising using background noise pickup subtraction to account for the presence of background magnetic fields.

13. The method of claim 10, comprising:
using an array of plural induction coils to detect the time varying magnetic field of a region of a subject's body; and further comprising:
using one or more of the coils of the array to detect the background magnetic field, and using the remaining coils of the array to detect the magnetic field of interest.

14. The method of claim 10, further comprising removing line frequency noise from the output signal for each coil before providing the output signal for analysis.

15. The method of claim 10, wherein the region of the subject's body whose magnetic field is being analysed comprises one of: the bladder, heart, head, brain, womb or a fetus.

16. A method of analysing the magnetic field of a subject's heart, the method comprising:
using the method of claim 10 to analyse the time varying magnetic field of a subject's heart.

17. A method, comprising:
using a magnetometer system for analysing magnetic field generated by a region of a subject's body,
the magnetometer system comprising one or more induction coils for detecting a time varying magnetic field and a detection circuit coupled to each coil and configured to convert a current or voltage generated in the coil by a time varying magnetic field to an output signal for use to analyse the time varying magnetic field, each coil having a maximum outer diameter of 4 to 7 cm, and a configuration such that the ratio of the coil's length to its outer diameter is in the range 0.5:1 to 0.8:1, and the ratio of the coil's inner diameter to its outer diameter is in the range 0.3:1 to 0.5:1.

* * * * *